(12) United States Patent
Lebens et al.

(10) Patent No.: US 9,506,891 B2
(45) Date of Patent: *Nov. 29, 2016

(54) MAKING IMPRINTED THIN-FILM ELECTRONIC SENSOR STRUCTURE

(71) Applicant: Eastman Kodak Company, Rochester, NY (US)

(72) Inventors: John Andrew Lebens, Rush, NY (US); Ronald Steven Cok, Rochester, NY (US); Yongcai Wang, Rochester, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 179 days.

This patent is subject to a terminal disclaimer.

(21) Appl. No.: 14/460,589

(22) Filed: Aug. 15, 2014

(65) Prior Publication Data

US 2016/0047772 A1    Feb. 18, 2016

(51) Int. Cl.
| | |
|---|---|
| *B05D 5/12* | (2006.01) |
| *G01N 27/403* | (2006.01) |
| *G06F 3/044* | (2006.01) |
| *H05K 3/46* | (2006.01) |
| *H05K 3/00* | (2006.01) |
| *H05K 3/10* | (2006.01) |
| *H05K 3/42* | (2006.01) |

(52) U.S. Cl.
CPC ............. *G01N 27/403* (2013.01); *G06F 3/044* (2013.01); *H05K 3/467* (2013.01); *B05D 5/12* (2013.01); *G06F 2203/04103* (2013.01); *G06F 2203/04112* (2013.01); *H05K 3/0011* (2013.01); *H05K 3/107* (2013.01); *H05K 3/42* (2013.01); *H05K 3/46* (2013.01)

(58) Field of Classification Search
USPC ...................................... 427/97.2, 97.7, 98.4
See application file for complete search history.

(56) References Cited

U.S. PATENT DOCUMENTS

| | | | |
|---|---|---|---|
| 5,337,018 A | 8/1994 | Yamagishi | |
| 6,730,212 B1 | 5/2004 | Yamagishi et al. | |
| 7,061,061 B2 * | 6/2006 | Goodman | G01N 33/0031 257/414 |
| 7,371,452 B2 * | 5/2008 | Bourdelais | G02B 6/1221 174/95 |
| 7,520,173 B2 | 4/2009 | Lee et al. | |
| 2005/0142345 A1 * | 6/2005 | Jayaraman | H05K 3/005 428/216 |

(Continued)

OTHER PUBLICATIONS

Mamishev et al, Interdigital Sensors and Transducers, Proceedings of the IEEE, vol. 92, No. 5, May 2004, pp. 804-845.

(Continued)

*Primary Examiner* — Brian K Talbot
(74) *Attorney, Agent, or Firm* — Raymond L. Owens; Kevin E. Spaulding

(57) ABSTRACT

A method of making an imprinted electronic sensor structure on a substrate for sensing an environmental factor includes coating, imprinting, and curing a curable layer on the substrate to form a plurality of spatially separated microchannels extending from the layer surface into the cured layer. First and second layers are located in each microchannel to form a multi-layer micro-wire. Either the first layer is a cured electrical conductor forming a conductive layer located only within the micro-channel and the second layer is a reactive layer or the first layer is a reactive layer and the second layer is a cured electrical conductor forming a conductive layer located only within the micro-channel. The reactive layer is exposed to the environmental factor and at least a portion of the reactive layer responds to the environmental factor.

19 Claims, 13 Drawing Sheets

(56) References Cited

U.S. PATENT DOCUMENTS

| | | | | |
|---|---|---|---|---|
| 2007/0095661 A1* | 5/2007 | Wang | ............ | C23C 14/0694 |
| | | | | 204/400 |
| 2007/0207297 A1* | 9/2007 | Lee | ............ | H05K 3/045 |
| | | | | 428/209 |
| 2009/0108455 A1* | 4/2009 | Gurumurthy | ........ | H01L 21/288 |
| | | | | 257/762 |
| 2010/0270057 A1* | 10/2010 | Yanagimoto | ........ | H05K 3/107 |
| | | | | 174/250 |
| 2011/0063776 A1* | 3/2011 | Byrne | ............ | H01F 17/0006 |
| | | | | 361/323 |
| 2012/0138336 A1* | 6/2012 | Watanabe | ........... | H05K 3/107 |
| | | | | 174/250 |
| 2012/0213975 A1 | 8/2012 | Naisby et al. | | |
| 2012/0305179 A1* | 12/2012 | Hondo | ............ | H05K 3/0014 |
| | | | | 156/272.8 |
| 2012/0327021 A1* | 12/2012 | Ryu | ............ | G06F 3/044 |
| | | | | 345/174 |
| 2013/0245412 A1* | 9/2013 | Rong | ............ | A61B 5/14532 |
| | | | | 600/347 |
| 2014/0205810 A1* | 7/2014 | Trauernicht | ........... | B05D 5/12 |
| | | | | 428/172 |

OTHER PUBLICATIONS

Park et al, Soft Artificial Skin With Multi-Modal Sensing Capability Using Embedded Liquid Conductors, IEEE Sensors, 2011, pp. 81-84.

Alam et al, Concrete Moisture Content Measurement Using Interdigitated Near-Field Sensors, IEEE Sensors Journal, vol. 10, No. 7 Jul. 2010, pp. 1243-1248.

Arshak et al, A review of gas sensors employed in electronic nose applications, Sensor Review, vol. 24, No. 2, 2004, pp. 181-198.

Yu et al, Microfabricated Thin Film Impedance Sensor & AC Impedance Measurements, Sensors 2010, 10, 5845-5858.

* cited by examiner

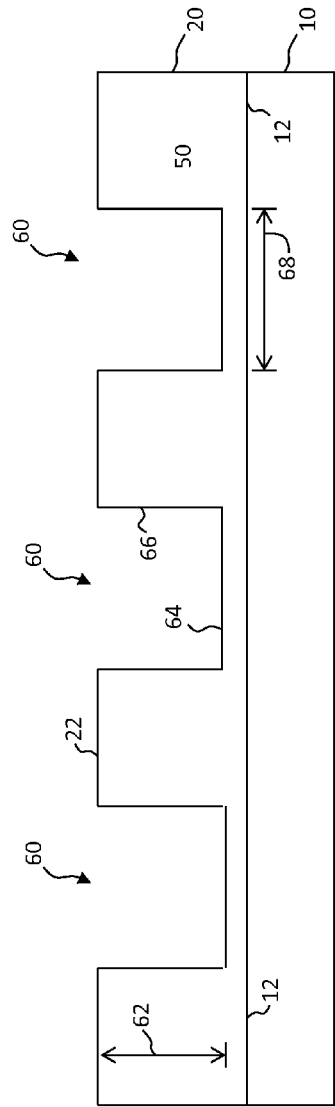
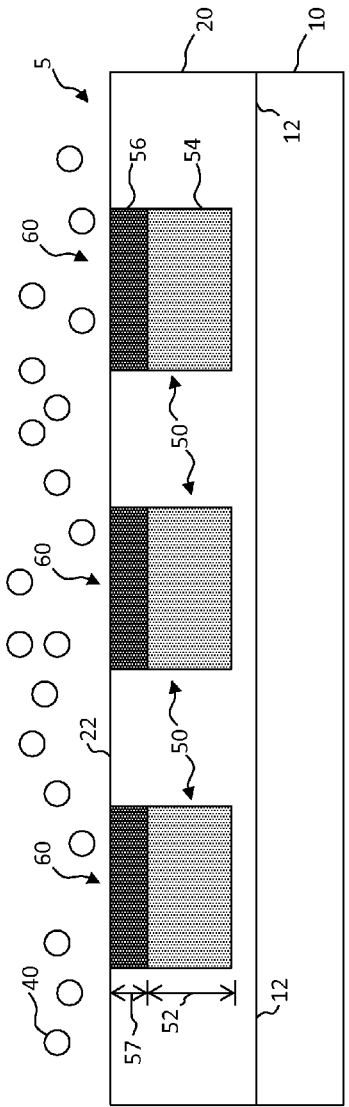
FIG. 1A
FIG. 1B

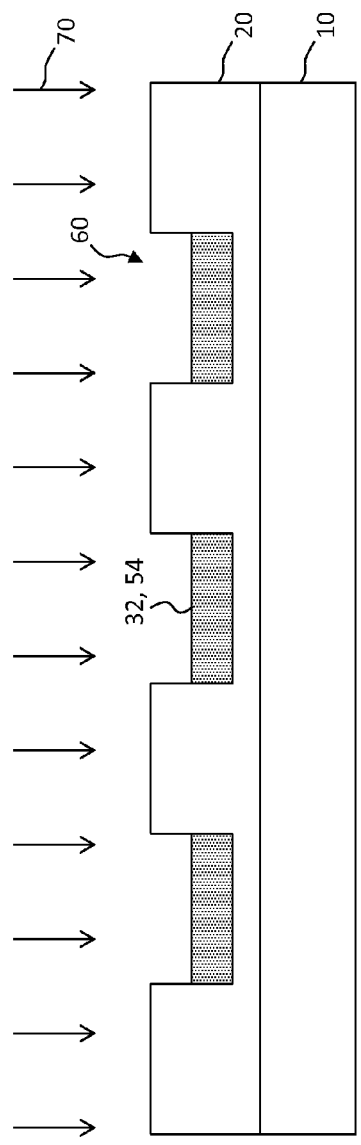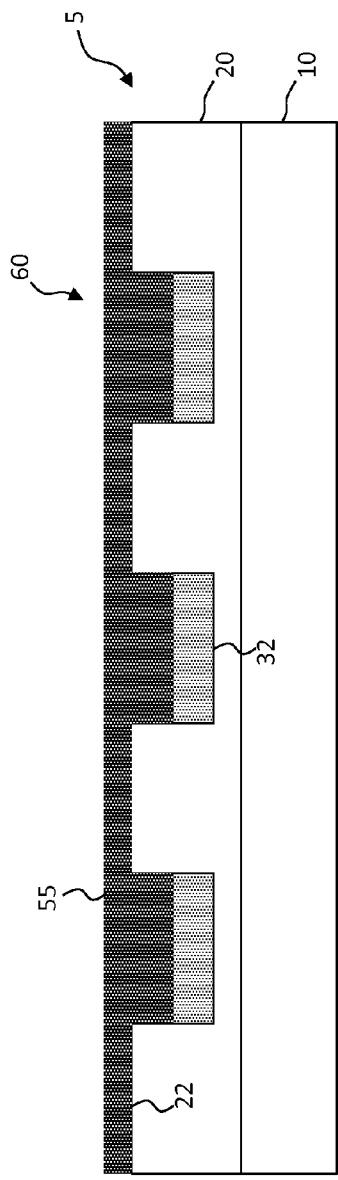

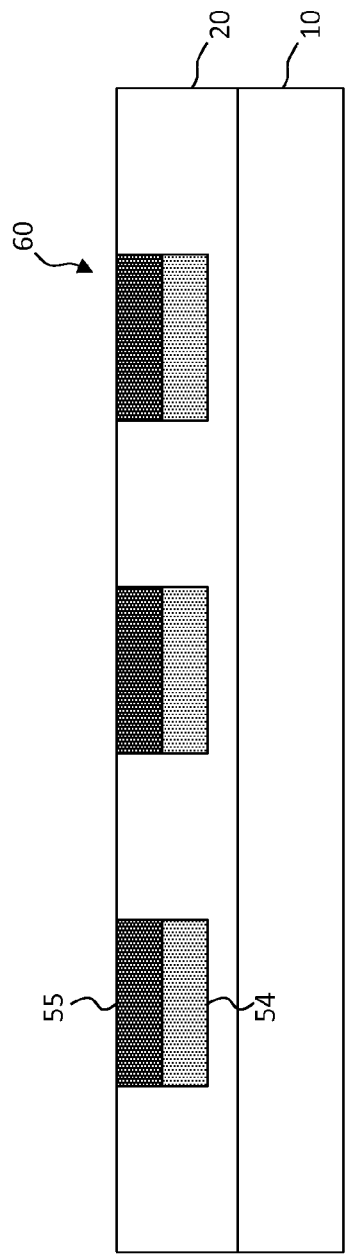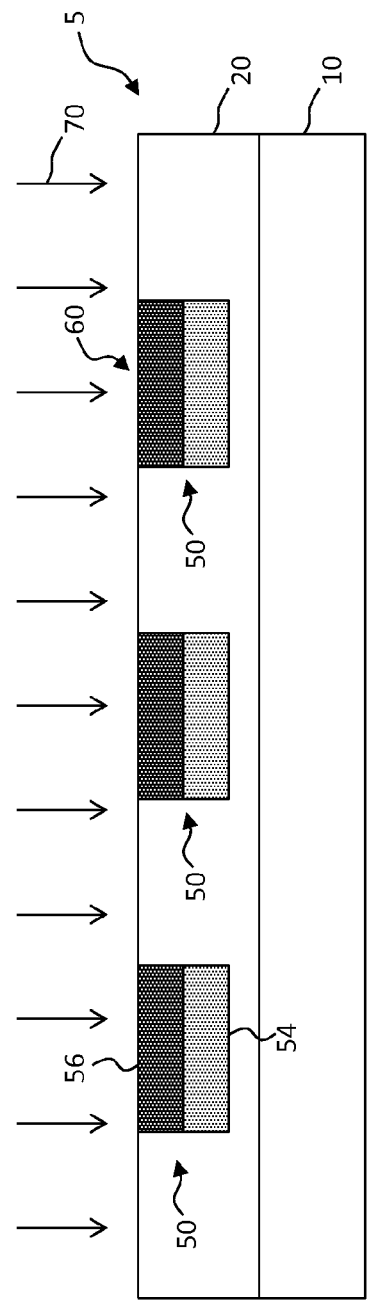

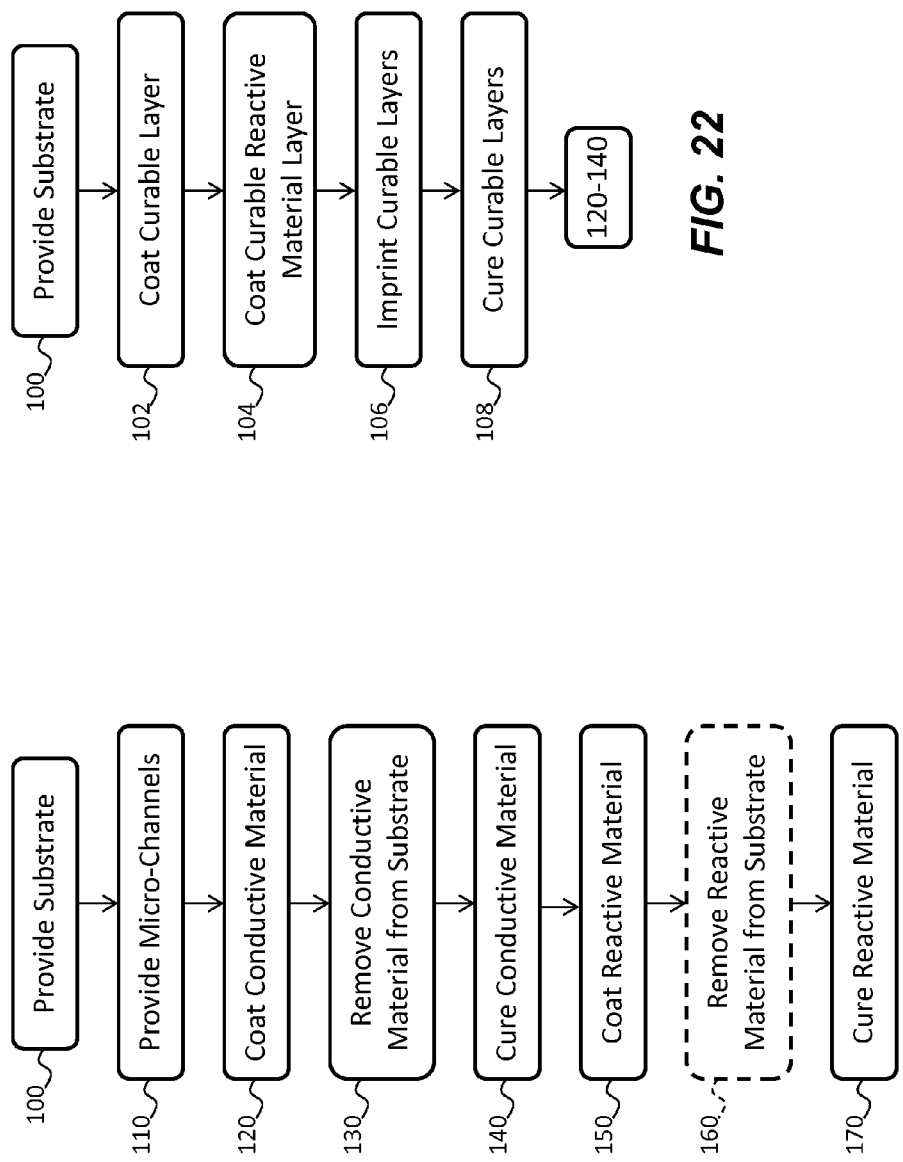

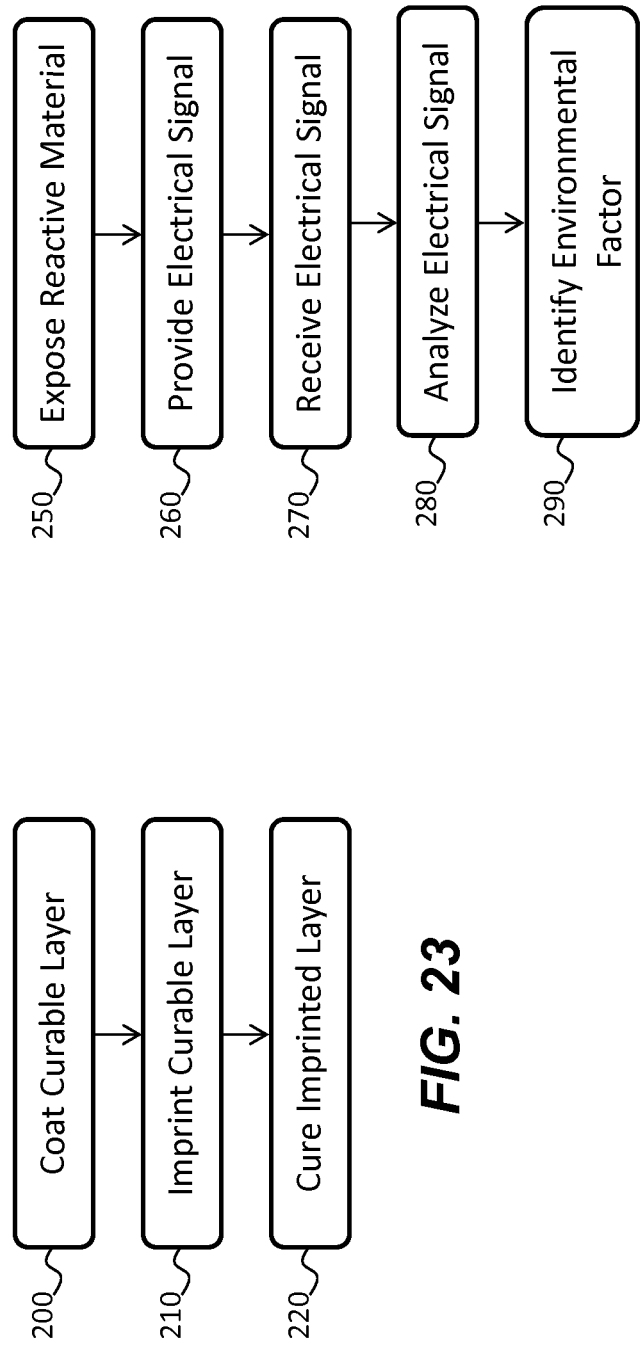

MAKING IMPRINTED THIN-FILM ELECTRONIC SENSOR STRUCTURE

CROSS REFERENCE TO RELATED APPLICATIONS

Reference is made to commonly-assigned co-pending U.S. patent application Ser. No. 14/460,589, herewith filed Aug. 15, 2014, entitled "Imprinted Thin-film Electronic Sensor Structure," by Lebens et al. (published as U.S. Patent Application Publication 2016/0047766), to commonly-assigned co-pending U.S. patent application Ser. No. 14/460,598, filed Aug. 15, 2014, entitled "Operating Imprinted Thin-film Electronic Sensor Structure," by Lebens et al. (published as U.S. Patent Application Publication 2016/0047767), and to commonly assigned U.S. patent application Ser. No. 13/779,939 filed Feb. 28, 2013, entitled "Making Multi-Layer Micro-Wire Structure," by Yau et al. (issued as U.S. Pat. No. 8,828,503), the disclosures of which are incorporated herein.

FIELD OF THE INVENTION

The present invention relates to electronic sensors imprinted in a substrate.

BACKGROUND OF THE INVENTION

Electronic sensors for detecting and evaluating materials such as liquids and gases found in the environment are known. Such an electronic sensor is sometimes called an "electronic nose" and is typically fabricated on a silicon substrate using conventional integrated circuit techniques at a relatively high cost. Electronic environmental sensors are widely useful in industrial systems and for measuring environmental contaminants.

A typical system includes a sensor portion that outputs electronic signals in response to an analyte. The electrical signals are filtered, amplified, and analyzed by a signal processor or other processing device or computer. The signal processing can be performed with computing circuits formed on the same substrate as the sensor. U.S. Pat. No. 5,337,018 illustrates an electronic sensor for determining alcohol content of fuels.

The sensor portion can include one or more spaced-apart electrodes in a variety of configurations. For example, U.S. Pat. No. 5,337,018 illustrates linear interdigitated electrodes and U.S. Pat. No. 7,520,173 illustrates electrodes formed in concentric circular or polygonal patterns. U.S. Pat. No. 6,730,212 discloses a sensor for chemical and biological materials that includes metal interdigitated electrodes coated with a hybrid polymer-base conducting film.

Electrode sensors are made using a variety of technologies including integrated circuit photolithographic methods, screen printing with thick films of silver and silver-palladium inks, electroplating to deposit a uniform layer of patterned copper, or by patterning sputtered or vaporized metal coating using laser ablation or photolithographic methods including liftoff and etching through a patterned mask layer. Photolithographic processes are known to be expensive, and generally require a rigid substrate for the formation of small feature size, e.g. <5 microns. Screen printing permits reliable formation of structures and patterns but only for a gap width or feature size of greater than 75 microns. Laser ablation or scribing uses a high-power excimer laser such as a Krypton-fluoride excimer laser having a wavelength of 248 nm to etch or scribe individual lines in the conductive surface metal coating to provide insulating gaps between residual conductive metal forming electrodes and other desired features. Laser ablation requires a time-consuming rastering technique if a complex electrode pattern is to be formed on the surface. Moreover, the precision of the electrode edge is not well defined. Sensor layers with embedded micro-channels are also known for pressure sensors.

Although electronic sensors are widely useful, the cost associated with the desired feature sizes can limit their applicability.

SUMMARY OF THE INVENTION

There remains a need, therefore, for further improvements in the manufacture and cost of electronic sensors.

In accordance with the present invention, a method of making an imprinted electronic sensor structure on a substrate for sensing an environmental factor comprises:

coating a curable layer on the substrate, imprinting the curable layer to form micro-channels in the curable layer, and curing the curable layer to form a plurality of spatially separated micro-channels extending from the layer surface into the cured layer;

locating a first layer in the micro-channels, and locating a second layer at least partly over the first layer to form a multi-layer micro-wire in each micro-channel, wherein either:

the step of locating a first layer in the micro-channels includes forming a cured electrical conductor as a conductive layer located only within the micro-channel and the step of locating a second layer at least partly over the first layer includes providing a second layer that is a reactive layer; or the step of locating a first layer in the micro-channels includes providing the first layer as a reactive layer and forming a cured electrical conductor as a conductive layer located only within the micro-channel; and exposing the reactive layer to the environmental factor and so that at least a portion of the reactive layer responds to the environmental factor.

The present invention provides a thin-film multi-layer micro-wire structure having improved conductivity, flexibility, and reduced manufacturing costs for an imprinted electronic sensor structure on a substrate that senses an environmental factor.

BRIEF DESCRIPTION OF THE DRAWINGS

The above and other features and advantages of the present invention will become more apparent when taken in conjunction with the following description and drawings wherein identical reference numerals have been used to designate identical features that are common to the figures, and wherein:

FIG. 1A is a cross section illustrating an imprinted substrate useful in understanding an embodiment of the present invention;

FIG. 1B is a cross section illustrating an embodiment of the present invention that corresponds to a portion of the cross section line B of FIG. 9;

FIGS. 10-18 are cross sections illustrating successive steps in a method of the present invention;

FIGS. 21-24 are flow diagrams illustrating methods of the present invention.

Figure 2B:
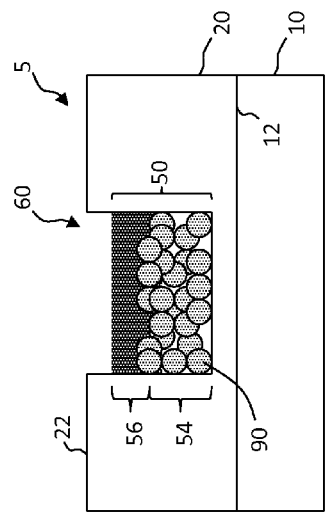
FIG. 2B is a cross section of FIG. 2A along the cross section line B and a portion of the cross section line B of FIG. 9.

The Figures are not drawn to scale since the variation in size of various elements in the Figures is too great to permit depiction to scale.

DETAILED DESCRIPTION OF THE INVENTION

The present invention provides an imprinted electronic sensor structure on a substrate for sensing an environmental factor. The imprinted electronic sensor structure includes a thin-film multi-layer micro-wire structure on a substrate that senses an environmental factor. In an embodiment, the thin-film multi-layer micro-wire structure is miniaturized with improved sensitivity, selectivity, and response time at reduced manufacturing costs.

Referring to FIGS. 1A and 1B, an imprinted electronic sensor structure 5 for sensing an environmental factor according to an embodiment of the present invention includes a substrate 10. A cured layer 20 has a layer surface 22 located on a substrate surface 12 of the substrate 10. A plurality of spatially separated micro-channels 60 extend from the layer surface 22 into the cured layer 20. Referring specifically to FIG. 1A, the micro-channels 60 are illustrated together with a micro-channel bottom 64, a micro-channel side 66, and a micro-channel width 68. The micro-channel 60 has a micro-channel depth 62 that, in an embodiment, has a depth less than 20 microns. Referring specifically to FIG. 1B, a multi-layer micro-wire 50 is formed in each micro-channel 60. The multi-layer micro-wire 50 includes at least a conductive layer 54 having a conductive layer depth 52 and a reactive layer 56 having a reactive layer depth 57. The reactive layer 56 is exposed to an environmental factor 40 and at least a portion of the reactive layer 56 responds to the environmental factor 40 so that the characteristics of the reactive layer 56 are changed by the environmental factor 40. The change in characteristics is measurable through the conductive layer 54, for example by measuring the capacitance or complex impedance between two adjacent multi-layer micro-wires 50. The layer surface 22 of the cured layer 20 can also interact to some extent with the environmental factor 40 and changes in the characteristics of the cured layer 20 are also detected through the conductive layer 54.

The conductive layer 54 is a cured electrical conductor located only within the micro-channel 60. The reactive layer 56 is located at least partly in the micro-channels 60 or completely in the micro-channels 60 (as shown in FIG. 1B). As illustrated in FIG. 1B, the reactive layer depth 57 is less than the conductive layer depth 52 and the reactive layer 56 is closer to the layer surface 22 than the conductive layer 54.

Figure 2C:
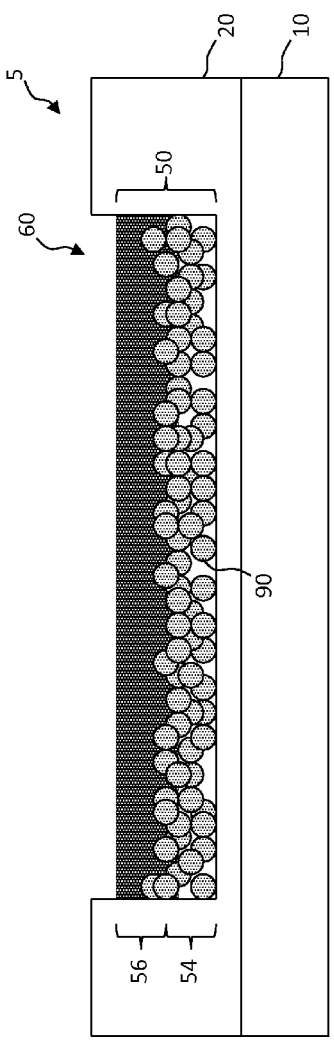
FIG. 2C is a cross section of FIG. 2A along the cross section line C and the cross section line C of FIG. 9.
Figure 2A:
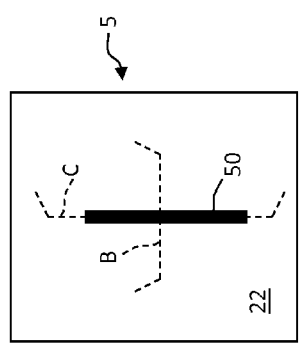
FIG. 2A is a plan view of a multi-layer micro-wire in an embodiment of the present invention.

Referring to the plan view of FIG. 2A, the multi-layer micro-wire 50 of the imprinted electronic sensor structure 5 includes cross section lines B and C corresponding to the cross sections of FIGS. 2B and 2C, respectively. Referring to FIGS. 2B and 2C, each micro-channel 60 formed in cured layer 20 on substrate 10 includes a multi-layer micro-wire 50. Each multi-layer micro-wire 50 includes the conductive layer 54 and the reactive layer 56. In an embodiment, the conductive layer 54 is a cured electrical conductor that includes metal particles 90 in the imprinted electronic sensor structure 5. The metal particles 90 can include silver and, in an embodiment, are cured, for example with heat to sinter, solder, or weld the metal particles 60 together to form the cured electrical conductor of conductive layer 54. Because the metal particles 90 do not necessarily form a completely uniform surface, the surface of the conductive layer 54 is somewhat irregular and the reactive layer 56 overlaps somewhat with the conductive layer 54. In various embodiments, the reactive layer 56 is a polymer or a metal.

Figure 3:
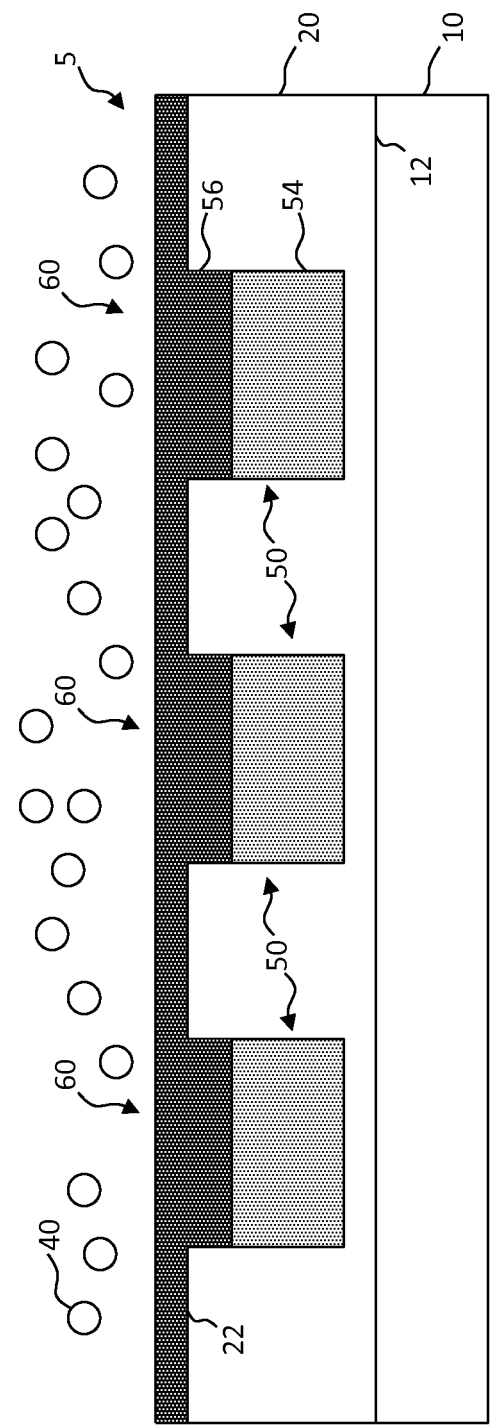
FIG. 3 is a cross section according to another embodiment of the present invention.

Referring next to FIG. 3, in an embodiment of the imprinted electronic sensor structure 5, the reactive layer 56 extends over the layer surface 22 outside the micro-channels 60 in the cured layer 20 on the substrate 10. In such an arrangement, the environmental factor 40 has a greater surface area of the reactive layer 56 with which to react, thus increasing the sensitivity of the device to the environmental factor 40. At the same time, the conductive layer 54 has a thickness greater than the thickness of the reactive layer 56 to improve the conductivity of the conductive layer 54, thereby also improving the quality of an electrical signal derived from the conductive layer 54 and reducing the signal-to-noise ratio of any measurements of the environmental factor 40 obtained from the multi-layer micro-wires 50 of the imprinted electronic sensor structure 5.

Figure 4:
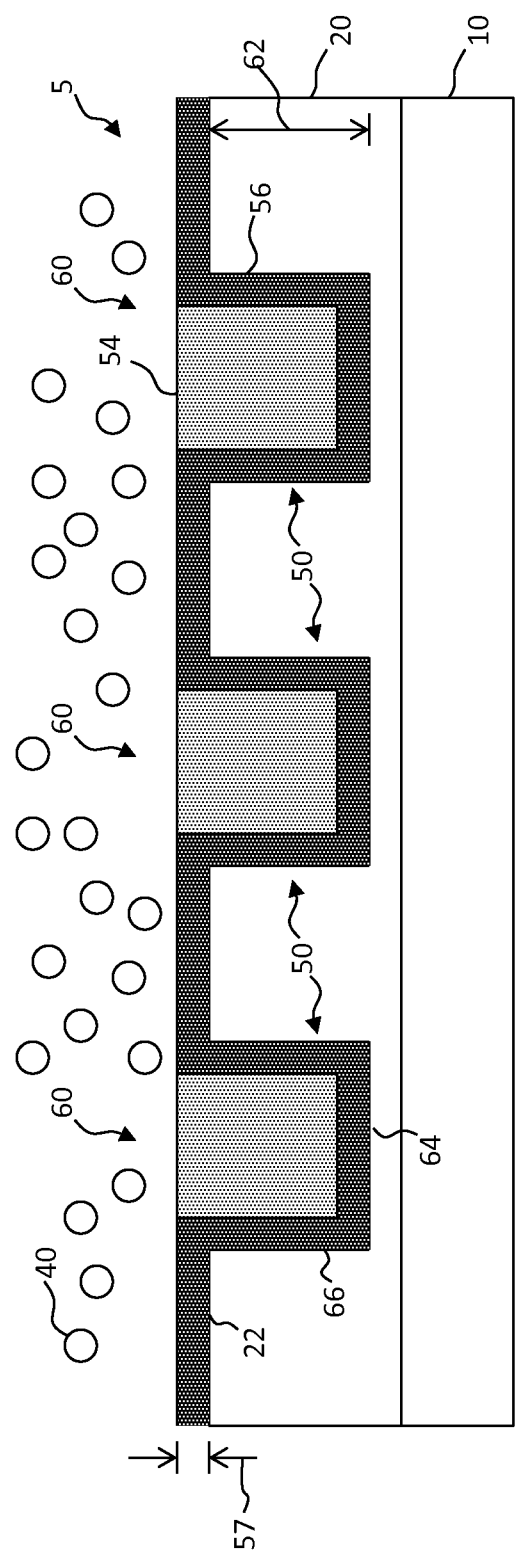
FIG. 4 is a cross section according to another embodiment of the present invention.

Referring next to FIG. 4, in an embodiment of the imprinted electronic sensor structure 5, the conductive layer 54 is closer to the layer surface 22 of the cured layer 20 on the substrate 10 than at least a portion of the reactive layer 56 within the micro-channel 60. As shown in FIG. 4, the micro-channels 60 have the micro-channel bottom 64 and micro-channel sides 66 and the reactive layer 56 extends over the micro-channel bottom 64, the micro-channel sides 66, and the layer surface 22 outside the micro-channels 60. The conductive layer 54 is above the reactive layer 56 in the micro-channel 60. This arrangement also increases the area of the reactive layer 56 on the layer surface 22 of the cured layer 20 that is exposed to the environmental factor 40 and the area of the reactive layer 56 in contact with the cured layer 20. Since some of the environmental factor 40 can pass through the reactive layer 56 into the cured layer 20 and then to the reactive layer 56 on the side walls of the micro-channels 60, an increased response is achievable with the configuration of FIG. 4. At the same time, the thickness of the conductive layer 54 is increased to further improve the conductivity of the conductive layer 54 and thereby improve the signal-to-noise ratio of any electrical signals measured by the multi-layer micro-wires 50.

In another embodiment of the present invention illustrated in FIG. 4, the imprinted electronic sensor structure 5 on the substrate 10 includes a first cured layer 20 having a layer surface 22 located on the substrate 10. A plurality of spatially separated micro-channels 60 extend from the layer surface 22 into the first cured layer 20. The micro-channels 60 have a micro-channel bottom 64 and micro-channel sides 66. A second cured layer 56, for example reactive layer 56, extends over the micro-channel bottom 64, the micro-channel sides 66, and the layer surface 22. In a further embodiment of the imprinted electronic sensor structure 5, the micro-channel depth 62 of the micro-channel 60 is greater than the thickness of the second cured layer 56.

Figure 5:
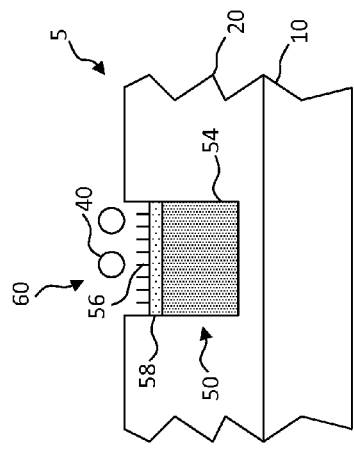
FIGS. 5-7 are cross sections of multi-layer micro-wires according to various embodiments of the present invention.

A further embodiment of the imprinted electronic sensor structure 5 of the present invention illustrated in FIG. 5 includes an inert layer 58 located between the conductive layer 54 and the reactive layer 56. The inert layer 58, the conductive layer 54, and the reactive layer 56 make up the multi-layer micro-wire 50 in the micro-channels 60 of the cured layer 20 on the substrate 10 in this embodiment. The inert layer 58 prevents chemical reactions between the reactive layer 56 and the conductive layer 54 and thus maintains the stability of the multi-layer micro-wire 50 and its performance. In an embodiment, the inert layer 58 is electrically conductive, for example the inert layer 58 is gold or includes gold. Gold is a useful material because it is relatively non-reactive to a wide variety of materials.

Figure 6:
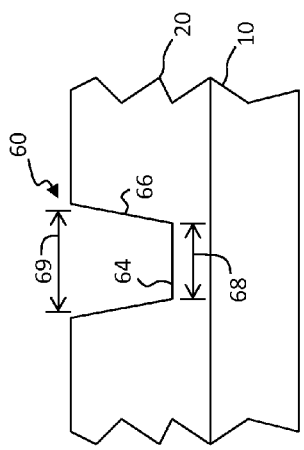

As schematically illustrated in the cross section of FIG. 6, in another embodiment of the imprinted electronic sensor structure 5, the reactive layer 56 is a functionalized layer that responds to a specific environmental factor 40. The inert layer 58 prevents the environmental factor 40 and the functionalized reactive layer 56 from affecting the conductive layer 54 of the multi-layer micro-wire 50 in the micro-channel 60 of the cured layer 20 on the substrate 10. The inert layer 58 can prevent electro-chemical interactions between the environmental factor 40 and the conductive layer 54 or between the reactive layer 56 and the conductive layer 54 that can deleteriously affect the conductivity of the conductive layer 54.

Figure 7:
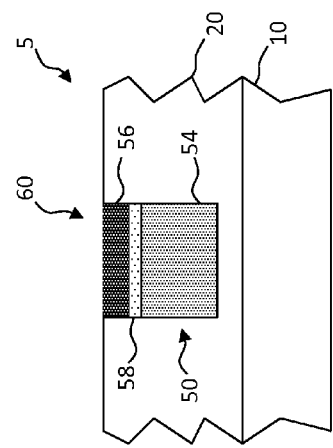

As shown in FIG. 1B, the conductive layer 54 is thicker than the reactive layer 56, in order to improve the conductivity of the conductive layer 54 and the electrical signal transmitted by the conductive layer 54. Referring to FIG. 7 in another embodiment of the imprinted electronic sensor structure 5, the reactive layer 56 is thicker than the conductive layer 54 of the multi-layer micro-wire 50 in the micro-channel 60 of the cured layer 20 on the substrate 10. In useful embodiments of the present invention, the change over time of the electrical attributes of the multi-layer micro-wire 50 is measured as the environmental factor 40 permeates the reactive layer 56. The change over time of the electrical attributes of the multi-layer micro-wire 50 is representative of the density or concentration of the environmental factor 40. A thicker reactive layer 56 enables permeation measurements over a longer time since it takes more time for an environmental factor 40 to permeate a thicker reactive layer 56.

Figure 8:
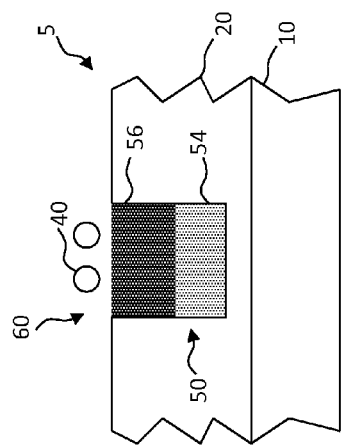
FIG. 8 is a cross section illustrating an imprinted substrate useful in understanding an embodiment of the present invention.

In embodiments of the present invention, a cross section of the micro-channel 60 is square or rectangular. In another embodiment, illustrated in FIG. 8, a cross section of the micro-channel 60 is not rectangular, for example trapezoidal. In this embodiment, the micro-channels 60 have the micro-channel bottom 64, a micro-channel top, and micro-channel sides 66 that are not perpendicular to the layer surface 22 of the cured layer 20 on the substrate 10. In the illustration of FIG. 8, the micro-channel 60 has a smaller micro-channel bottom 64 surface area than a surface area at the top of the micro-channel 60. As shown in FIG. 8, the micro-channel width 68 of the micro-channel 60 at the micro-channel bottom 64 is less than a micro-channel top width 69 of the micro-channel 60. Thus, in an embodiment, the reactive layer 56 is wider than the conductive layer 54 (not shown). This arrangement can increase the relative area of the reactive layer 56 and the density of the multi-layer micro-wires 50 in the cured layer 20.

In various embodiments of the present invention, the response of the reactive layer 56 is an electrical response, an amperometric response, or a change in resistivity, conductivity, dielectric constant, absolute permittivity, or relative permittivity. The reactive layer 56 can include one or more of a polymer, polymer composites, enzymes, carbon nanotubes, functionalized carbon nanotubes, grapheme, functionalized graphene, thiol groups, amine groups, carboxylic groups, nano-particles, conductive nano-particles, or magnetic nano-particles. In an embodiment, the reactive layer 56 is a cured polymer. In various embodiments, the environmental factor 40 is a chemical, is heat, is moisture, is radiation, is a biological material, or is combinations thereof.

For example, the reactive layer 56 is an ion-selective layer or multilayer comprising an ion-selective membrane, or a layer containing a fixed amount of ions, for example, chloride. In an embodiment, the environmental factor 40 is body sweat. In this configuration the imprinted electronic sensor can be used for sweat monitoring, for example to alert a subject of dehydration, or to detect drug abuse.

The reactive layer 56 is a functionalized layer having a bio-recognition element (generally antibody or nucleic acid). Different surface modification techniques can be used for the immobilization of bio-recognition elements on the surface of electrodes. For example the reactive layer 5 can be a plated gold layer over the conductive layer 54 or over an inert layer 58. The gold surface is immobilized with antibodies by silanizing the gold surface using 3-mercaptomethyldimethylethoxysilane and a hetero-bifunctional cross-linker, N-(g-maleimidobutyryloxy) succinimide ester. The imprinted electronic sensor in this configuration can be used to detect, for example, bacteria such as *E. coli* cells suspended in peptone water through impedance measurements. In other embodiments, a plated gold layer serves as an inert layer 58.

In an embodiment, the reactive layer 56 is a passivation layer, for example, a plated gold layer that improves the corrosion resistance of the multi-layer micro-wires 50 if they are made out silver. The leached silver ions can potentially kill bacteria and is of interest for analysis. An imprinted electronic sensor of this type is useful to detect changes based on metabolites produced by bacterial cells as a result of growth. The growth of micro-organisms normally increases the conductivity of the medium by converting uncharged or weakly charged substances present in the growth medium, such as yeast, peptone, and sugar, into highly charged substances such as amino acids, aldehydes, acids, and other metabolic products.

The reactive layer 56 is a film material that can have a high sensitivity to water vapor with a linear response from 0% to 100% RH, short response time, high selectivity (i.e., low or no cross-sensitivity), and high long-term stability. Sensitive films can be fabricated from material such as porous ceramics, polymers, or polyelectrolytes.

In an embodiment, the reactive layer 56 is a solid electrolyte such as NASICON for carbon dioxide detection, or a polymer layer doped with conductive particles which changes its electrical resistance in response to an organic volatiles for VOC detection. The polymer can be chosen according to the type of organic vapor for selectivity.

In another embodiment of the present invention, the imprinted electronic sensor structure 5 on the substrate 10 includes the first cured layer 20 having the layer surface 22 located on the substrate 10. A plurality of spatially separated micro-channels 60 extend from the layer surface 22 into the cured layer 20. The micro-channels 60 have a micro-channel bottom 64 and micro-channel sides 66. A second cured layer, for example reactive layer 56, extends over the micro-channel bottom 64, the micro-channel sides 66, and the layer surface 22. In a further embodiment of the imprinted electronic sensor structure 5, the micro-channel depth 62 of the micro-channel 60 is greater than the thickness of the second cured layer 56.

Figure 9:
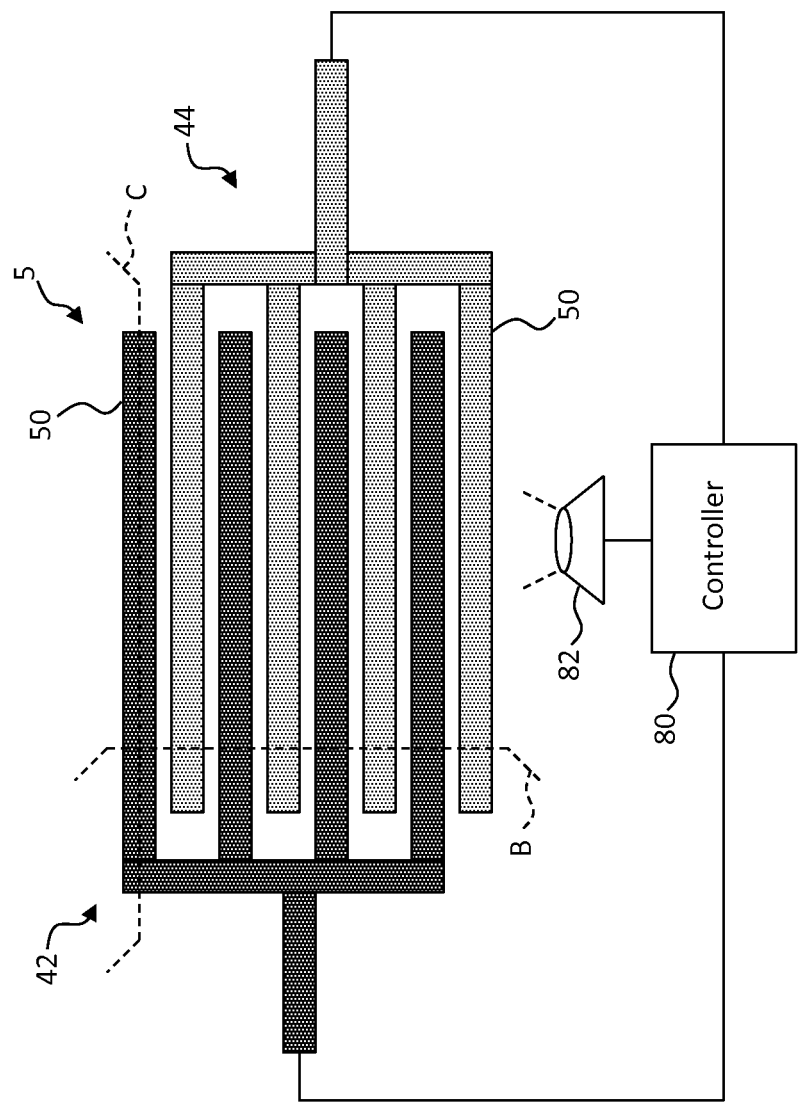
FIG. 9 is a schematic of an embodiment of the present invention having a controller for controlling interdigitated multi-layer micro-wires.
Figure 10:
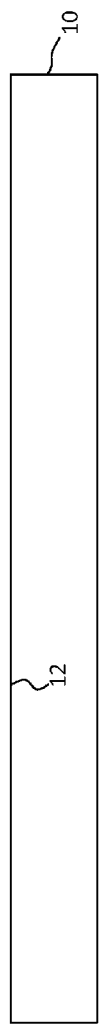
Figure 11:
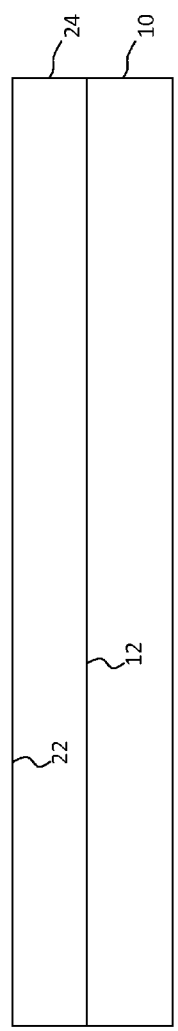
Figure 12:
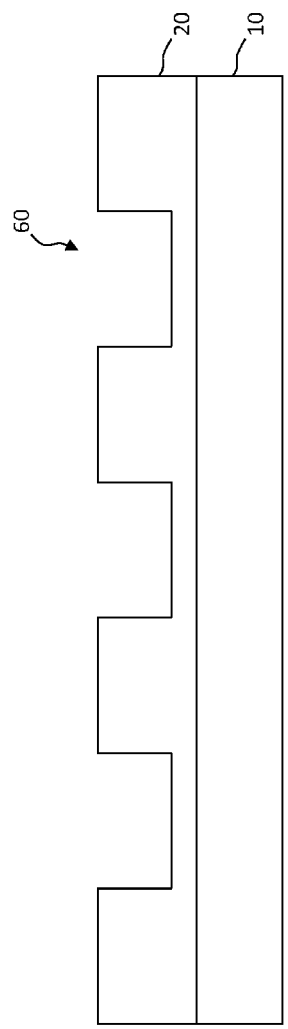

Referring next to FIG. 9 in an embodiment of the imprinted electronic sensor structure 5, the multi-layer micro-wires 50 are grouped into a first group 42 of multi-layer micro-wires 50 and a second group 44 of multi-layer micro-wires 50 different from the multi-layer micro-wires 50 of the first group 42. The multi-layer micro-wires 50 of each group are electrically connected and the multi-layer micro-wires 50 of the first group 42 are interdigitated with the multi-layer micro-wires 50 of the second group 44. A controller 80 electrically controls the first and second groups 42, 44 of multi-layer micro-wires 50 to electrically detect changes in the imprinted electronic sensor structure 5, for example from interactions between the environmental factor 40 (not shown) and the reactive layer 56 (not shown) of the multi-layer micro-wires 50.

An aspect of the invention relates to the interdigitated microelectrode array in combination with a flexible substrate. The array includes a working electrode and a counter electrode, each including a common lead and commonly-connected electrode elements with the electrode elements being arranged in a substantially parallel, alternating fashion. The microelectrode can have a width in the range of from 2 to 100 microns. The spacing between the microelectrodes can be in the range of from 2 to 50 microns. In order to have good sensitivity and proper amplification for sensing, the interdigitated microelectrode array can have as many pairs of microelectrodes (working and counter electrode) as desired. Amplification in general increases with decreased width and spacing of the microelectrodes and increased length and number of microelectrode pairs. The interdigitated microelectrode array can also include a reference electrode.

The interdigitated microelectrode array is useful as an electrochemical sensor. A significant advantage of the present invention over the methods described in the prior art (e.g. laser ablation) is that the width and spacing of the microelectrode can be made very small, e.g. 2 to 10 microns, on a flexible substrate at reduced cost due to the simplicity of the manufacturing process and without sacrificing the quality of microelectrode dimension and spacing uniformity. Therefore the imprinted electronic sensor structure 5 provided by the present invention enables an accurate and precise readout from a relatively small analyte sample size, for example, less than 1 µL or less than 0.5 µL. In addition, the imprinted electronic sensor structure 5 as manufactured by a method of the present invention can have significantly improved diffusion recycling efficiency that enables highly sensitive electrochemical measurements with a high signal-to-noise ratio and a wide dynamic range.

The interdigitated microelectrode array can have a chemical coating deposited over the array to facilitate the practice of electrochemical detection. The chemical coating can contain a chemical reactive to produce an electro-active reaction product. Upon contacting the coating with a sample that contains an analyte, the analyte reacts with chemical compounds of the coating to generate an electro-active reaction product. This electro-active reaction product can be electronically detected, measured, or quantified by applying a potential difference between the electrodes and measuring the current at the working electrode.

In contrast to the thin-film electrical conductors of the present invention, thick-film conductors of the prior art, for example formed by processes such as screen printing silver paste, are not formed within the micro-channels 60 and are often limited in their width to widths that are directly visible to the unaided human visual system. Thus, the number of electrode sensors per linear area (as shown in FIG. 9, is smaller using such prior art methods than is enabled by embodiments of the present invention. An advantage of the present invention, therefore, is a greater electrode spatial resolution and a more sensitive electronic sensor at a lower cost.

In yet another embodiment, the imprinted electronic sensor structure 5 further includes an optical sensor 82 for sensing the optical state of the multi-layer micro-wires 50. In an embodiment, the optical state is combined with electrical signals derived by the controller 80 from the multi-layer micro-wires 50 to provide further information about the environmental factor 40. In an embodiment, the environmental factor 40 includes multiple environmental materials.

Referring to the successive cross sections of FIGS. 10-18 and the corresponding flow diagrams of FIGS. 21 and 23, a method according to the present invention of making the imprinted electronic sensor structure 5 includes providing the substrate 10 having the substrate surface 12 (FIG. 10) in step 100. Micro-channels 60 are then provided in step 110 by coating a curable layer 24 having the layer surface 22 on the substrate surface 12 of the substrate 10 in step 200 (FIGS. 11 and 23), imprinting the curable layer 24 in step 210, and curing the curable layer 24 in step 220 to form the cured layer 20 with a plurality of spatially separated imprinted micro-channels 60 on the substrate 10 (FIG. 12) extending from the layer surface 22 into the cured layer 20. Methods and materials for coating a single curable layer, imprinting the curable layer, and curing the curable layer are known in the art.

Figure 13:
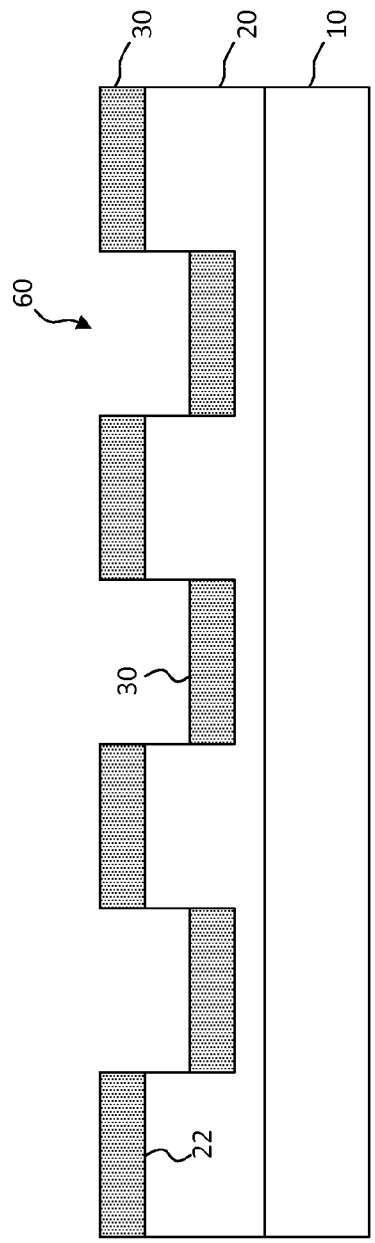
Figure 14:
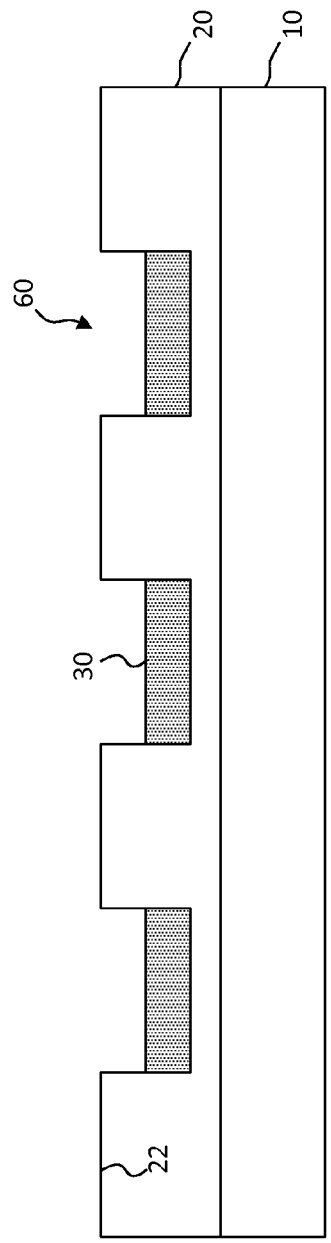
Figure 19:
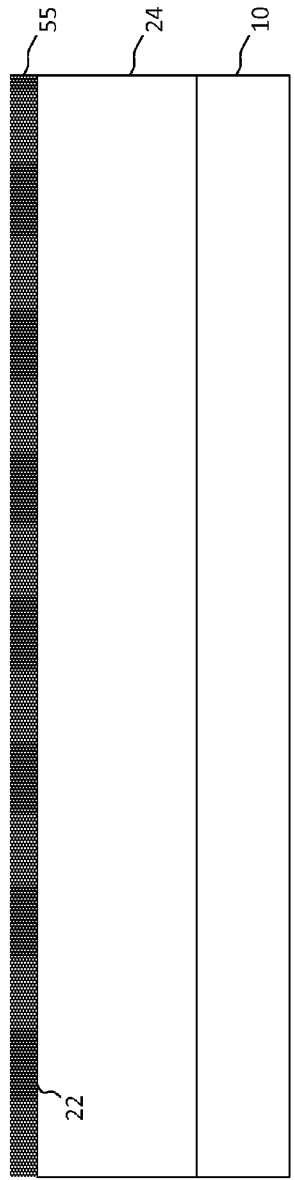
FIGS. 19-20 are cross sections illustrating successive steps in another method of the present invention.

Referring next to FIGS. 13 and 21, a conductive material, in this case a curable conductive ink 30 is coated on the layer surface 22 of the cured layer 20 on the substrate 10 and in the micro-channels 60 in step 120. The curable conductive ink 30 is removed from the layer surface 22 of the cured layer 20 on the substrate 10 in step 130 (FIG. 14) leaving the curable conductive ink 30 in the micro-channels 60. Referring to FIG. 15, ultra-violet radiation 70 (or heat) cures the curable conductive ink 30 (FIG. 14) to form cured conductive ink 32 in the micro-channels 60 in the cured layer 20 on the substrate 10 in step 140. In this embodiment, the cured conductive ink 32 forms the conductive layer 54. In step 150, referring to FIG. 16, the conductive layer 54 in the micro-channels 60 and the layer surface 22 of the cured layer 20 on substrate 10 are coated (step 150) with a curable reactive material 55. In an optional step 160 similar to step 130, the curable reactive material 55 is removed from the layer surface 22 of the cured layer 20 on the substrate 10 (FIG. 17). As shown in FIG. 18, the curable reactive material 55 is cured in step 170 to form the cured reactive layer 56 with ultra-violet radiation 70 (or heat) to form the multi-layer micro-wires 50 in the cured layer 20 on the substrate 10. If the optional step 160 of removing, the curable reactive material 55 from the layer surface 22 is omitted, the structure illustrated in FIG. 3 is obtained.

In one embodiment, the conductive layer 54 is a cured electrical conductor forming a first layer located only within the micro-channel and the reactive layer 56 is a second layer and the second layer is at least partly over the first layer and at least partly in the micro-channel. Alternatively, the reactive layer 56 forms a first layer and the conductive layer 54 is a second layer located only within the micro-channel. Thus, in a method of the present invention, locating the first and second layers on the substrate 10 includes locating the first layer, curing the first layer, locating the second layer over the first layer, and curing the second layer so that the conductive layer 54 is closer to the layer surface 22 than the reactive layer 56. Alternatively, locating the first and second layers includes locating the first layer, curing the first layer, locating the second layer over the first layer, and curing the second layer so that the reactive layer 56 is closer to the layer surface than the conductive layer 54.

Figure 20:
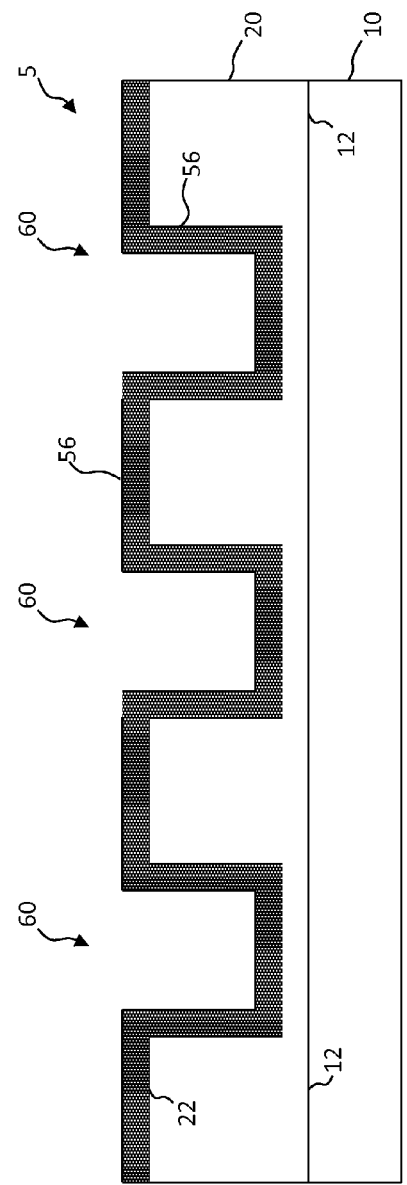

In an alternative embodiment, referring to FIGS. 10, 11, 18, and 19 and the flow diagram of FIG. 22, the substrate 10 is provided in step 100 (FIG. 10), the curable layer 24 is coated on the substrate surface 12 of the substrate 10 in step 102 (FIG. 11), the curable reactive material 55 is coated in a layer on the layer surface 22 of the curable layer 24 on the substrate 10 in step 104 (FIG. 18), and the curable layer 24 and the curable reactive material 55 layer are imprinted in step 106 and cured in a common step 108 (FIG. 20) using the same steps as discussed above to form the micro-channels 60 in the cured layer 20 on the substrate 10. It has been demonstrated that separate uncured layers are coated sequentially on the substrate surface 12 and imprinted and cured in common step to form the structure of FIG. 20. The steps 120-140 are then used as described above to form the conductive layer 54 and reactive layer 56.

Thus, in a method of the present invention, locating the first and second layers includes coating the substrate with the curable layer 24, coating the curable layer 24 with a second curable layer, imprinting the curable layer 24 and the second curable layer in a common step with a common imprinting stamp, and curing the curable layer and the second curable layer in a common step to form the micro-channels in the cured layer and the second layer, the first layer extending over the micro-channel bottom, the micro-channel sides, and the substrate surface outside the micro-channels. In an embodiment, the second layer is the reactive layer 56. In a further embodiment, locating the second layer includes coating the second layer over the substrate surface 12 and the micro-channels 60 so that the reactive layer 56 extends over the substrate surface 12 outside the micro-channels 60.

Alternatively, a method of the present invention includes coating a first curable layer on the substrate 10, coating a second curable layer on the first curable layer, imprinting the first curable layer and the second curable layer with a micro-channel stamp in a common step to form micro-channels 60 in the first curable layer and the second curable layer, and curing the first curable layer and the second curable layer in a common step to form one or more micro-channels 60 in the cured first layer and in the cured second layer.

Referring next to FIG. 24, the reactive layer 56 is exposed in step 250 to the environment factor 40 and at least a portion of the reactive layer 56 responds to the environmental factor 40. The controller 80 provides electrical signals to the first group of multi-layer micro-wires 42 in step 260 and receives them from the second group 44 of multi-layer micro-wires 44 in step 270. The received electrical signals are analyzed in step 280 to identify the environmental factor 40 in step 290. In an embodiment, the analysis and identification is done with the controller or, in an alternative embodiment, with an external computer. Useful controllers 80 or computers are known in the art.

Another method of the present invention includes forming an inert layer 58 located between the conductive layer 54 and the reactive layer 56. The inert layer 58 prevents chemical reactions between the reactive layer 56 and the conductive layer 54. The inert layer can include gold. A useful method can further include functionalizing a surface of the inert layer 58 to provide the reactive layer 56 that is reactive to a specific environmental factor 40.

Further methods of the present invention include coating a conductive ink with metal particles 90 in the micro-channels 60 and curing the conductive ink to form the conductive layer 54.

Other methods of the present invention include grouping the multi-layer micro-wires 50 into the first group 42 of multi-layer micro-wires 50 and the second group 44 of multi-layer micro-wires 50 different from the multi-layer micro-wires 50 of the first group 42, the first group 42 of multi-layer micro-wires 50 is interdigitated with the second group 44 of multi-layer micro-wires 50, the first group 42 of multi-layer micro-wires 50 are electrically connected, and the second group 44 of multi-layer micro-wires 50 are electrically connected, providing the controller 80 for electrically controlling the first and second groups 42, 44 of multi-layer micro-wires 50, and using the controller 80 to measure the electrical response of the first and second groups 42, 44 of multi-layer micro-wires 50. The electrical response can include one or more of the amperometric response, the resistance, the capacitance, the impedance, the complex impedance, or the inductance.

In a further embodiment of the present invention, the step 250 of exposing the reactive layer 56 to the environmental factor 40 includes exposing the reactive layer 56 to a liquid or to a gas. In yet another embodiment, an optical sensor is provided for sensing the optical state of the multi-layer micro-wires 50 and optically sensing the optical state of the multi-layer micro-wires 50.

Another embodiment of the present invention includes measuring a first electrical response of the multi-layer micro-wire 50 at a first time, measuring a second electrical response of the multi-layer micro-wire 50 at a second time later than the first time, and comparing the first electrical response to the second electrical response to determine a change in the environmental factor 40, to determine a concentration of the environmental factor 40, or to determine a change in the reactive layer 56 in response to the environmental factor 40, for example using the controller 80. In various embodiments, the response is a change in conductivity, dielectric constant, absolute permittivity, or relative permittivity of the reactive layer 56, the environmental factor 40, the, cured layer 20, or the environment exterior to the imprinted electronic sensor structure 5.

The steps illustrated in FIGS. 10-20 are suitable for roll-to-roll manufacturing and are additive in nature and are therefore amenable to low-cost manufacturing. Thus, the present invention provides the imprinted electronic sensor 5 having improved conductivity, flexibility, transparency, and reduced manufacturing costs.

Structures of the present invention have been constructed and environmental factors 40 detected, for example include water vapor, water, alcohol, and methane.

The micro-channels 60 each include the multi-layer micro-wire 50 having a multi-layer micro-wire thickness less than or equal to 20 microns. In various embodiments, the conductive layer depth 52 is the average thickness of the conductive layer 54 or the maximum thickness of the conductive layer 54. Likewise, the reactive layer depth 57 is the average thickness of the reactive layer 56 or the maximum thickness of the reactive layer 56. The conductive layer 54 includes silver nano-particles 90 that are agglomerated, sintered, welded, soldered, or otherwise electrically connected to form the electrically conductive layer 54. The silver nano-particles 90 are regularly or randomly arranged in the micro-channel 60 and therefore the conductive layer 54 can have a variable conductive layer depth 52 along the micro-channel length as well as a variable conductive layer depth 52 across the micro-channel width 68. The conductive layer 54 can have a percent ratio of silver that is greater than or equal to 40% by weight.

In an embodiment, the silver nano-particles 90 are provided in an aqueous dispersion, in a liquid such as a solvent, or as a dry mixture and located in the micro-channels 60, for example by coating the substrate surface 12 and the micro-channels 60 (e.g. by spray or surface coating using methods known in the art) and then removed from the cured layer surface 22 (for example by scraping or wiping the cured layer surface 22), leaving the silver nano-particles 90 in the micro-channels 60 only. The dispersion can include other conductive or non-conductive materials, such as surfactants, anti-coagulants, anti-flocculants or other materials to improve the coatability of the liquid dispersion or dry materials. Once the silver nano-particles 90 are only located in the micro-channels 60, the dispersion is cured, for example with heat or evaporation to form a cured electrically conductive micro-wire having sintered or welded particles 90 that is the conductive layer 54. In an embodiment, other additional steps are employed to improve the electrical, optical or mechanical properties of the conductive layer 54, for example exposure to a hydrochloric vapor. The conductive layer 54 of the present invention can have a percent ratio of silver that is greater than or equal to 40% by weight after curing, drying, or other processing steps that render the silver nano-particle 90 dispersion electrically conductive. In other embodiments, the conductive layer 54 is equal to or greater than 50%, 60%, 70%, 80%, or 90% silver by weight.

In various embodiments, the multi-layer micro-wire 50 has a micro-wire width of twenty microns, ten microns, five microns, two microns, or one micron or less but greater than zero microns, a multi-layer micro-wire depth (thickness) equal to or less than twenty microns, ten microns, five microns, two microns, or one micron but greater than zero microns, and micro-wire lengths greater than or equal to 1 cm, 2 cm, 5 cm, 10 cm, 25 cm, 50 cm, 100 cm, 1 m, 2 m, 5 m, 10 m, or more.

In an embodiment, the conductive layer 54 is plated to improve its conductivity and robustness. In another embodiment, the inert layer 58 is plated on the conductive layer 54, for example by electroless plating.

In general, electroless plating processes are known. In an embodiment of the present invention, a useful autocatalytic process for forming an electrolessly plated inert layer 58 of the present invention includes a solution that includes metal or metal alloys. The conductive layer 54 is exposed to electroless plating at a plating station after the conductive layer 54 is formed. The plating station can include a tank that contains copper in a liquid state at a temperature range between 20° C. and 90° C. Alternatively, the conductive material can include at least one of silver (Ag), gold (Au), nickel (Ni), tin (Sn), and palladium (Pd), aluminum (Al), zinc (Zn), or combinations or alloys thereof. In an embodiment, the deposition rate is about 10 nanometers or more per minute (nm/min) and the plating station deposits the conductive material to a thickness of about 0.001 micrometer to about 6 micrometers according to the application. This electroless plating process does not require the application of an electrical current and it only plates the patterned areas containing the conductive layer 54. The plating thickness resulting from electroless plating is more uniform compared to electroplating due to the absence of electric fields. Although electroless plating is more time consuming than electrolytic plating, electroless plating is well suited for the many fine features that are present in a high-resolution conducting pattern of the conductive layers 54. After metal plating, the plated layer is rinsed with water to remove any residual plating solution and dried.

The present invention is useful for forming thin-film electrical conductors that are difficult to see with the unaided human visual system and therefore in some embodiments arrangements of the thin-film multi-layer micro-wires 50 of the present invention are apparently transparent. Not only are the thin-film multi-layer micro-wires 50 less than or equal to 20 microns thick in some embodiments, they are also located within the micro-channels 60 and are therefore limited in their width by the micro-channel width 68 to a width that is less than or equal to 20 microns. In other embodiments, the micro-channels 60 and the thin-film multi-layer micro-wires 50 of the present invention are less than or equal to 15 microns wide, less than or equal to 10 microns wide, less than or equal to 5 microns wide, less than or equal to 2 microns wide, or less than or equal to 1 micron wide and are therefore not directly perceptible by the unaided human visual system.

Curable layer materials, masks, exposure patterning through a mask, and etching methods are known in the art. In another embodiment, the layer is first formed as the curable layer 24, imprinted with a stamp, and then cured to form the cured layer 20 having the micro-channels 60. Curable materials, imprinting stamps, and curing methods are also known in the art.

According to various embodiments of the present invention, the substrate 10 is any material on which the cured layer 20 is formed. The substrate 10 is a rigid or a flexible substrate 10 made of, for example, a glass, metal, plastic, or polymer material, can be transparent, and can have opposing substantially parallel and extensive surfaces. The substrates 10 can include a dielectric material and can have a wide variety of thicknesses, for example 10 microns, 50 microns, 100 microns, 1 mm, or more. In various embodiments of the present invention, substrates 10 are provided as a separate structure or are coated on another underlying substrate, for example by coating a polymer substrate layer on an underlying glass substrate.

In various embodiments the substrate 10 is an element of other devices, for example the cover or substrate of a display or a substrate of an RFID device. In an embodiment, the substrate 10 of the present invention is large enough for a user to directly interact therewith. Methods are known in the art for providing suitable surfaces on which to coat or otherwise form layers. In a useful embodiment, the substrate 10 is substantially transparent, for example having a transparency of greater than 90%, 80%, 70%, or 50% in the visible range of electromagnetic radiation.

The micro-channel 60 is a groove, trench, or channel formed on or in the cured layer 20 extending from the layer surface 22 of the cured layer 20 and having a cross-sectional width for example less than 20 microns, 10 microns, 5 microns, 4 microns, 3 microns, 2 microns, 1 micron, or 0.5 microns, or less. In an embodiment, the cross-sectional depth of the micro-channel 60 is comparable to its width. Micro-channels 60 can have a rectangular cross section. Other cross-sectional shapes, for example trapezoids, are known and are included in the present invention. The width or depth of a layer is measured in cross section.

In various embodiments of the present invention, the multi-layer micro-wires 50 at least partially fill the micro-channels 60, have a width less than or equal to 10 microns, 5 microns, 4 microns, 3 microns, 2 microns, or 1 micron. In an example and non-limiting embodiment of the present invention, each multi-layer micro-wire 50 is from 10 to 15 microns wide, from 5 to 10 microns wide, or from 5 microns to one micron wide. In an embodiment, the multi-layer micro-wires 50 are solid; in another embodiment, the multi-layer micro-wires 50 are porous.

In various methods, a variety of multi-layer micro-wire 50 patterns are used and the present invention is not limited to any one pattern. Micro-channels 60 can be identical or have different sizes, aspect ratios, or shapes. Similarly, thin-film multi-layer micro-wires 50 can be identical or have different sizes, aspect ratios, or shapes. The thin-film multi-layer micro-wires 50 can be straight or curved.

Imprinted cured layers 20 useful in the present invention can include a cured polymer material with cross-linking agents that are sensitive to heat or radiation, for example infra-red, visible light, or ultra-violet radiation. The polymer material is a curable material applied in a liquid form that hardens when the cross-linking agents are activated. When a molding device, such as an imprinting stamp having an inverse micro-channel structure is applied to liquid curable material and the cross-linking agents in the curable material are activated, the liquid curable material in the curable layer 24 is hardened into the cured layer 20 with imprinted micro-channels. The liquid curable materials can include a surfactant to assist in controlling coating. Materials, tools, and methods are known for embossing coated liquid curable materials to form cured layers.

The cured layer 20 is the curable layer 24 of curable material that has been cured. For example, the cured layer 20 is formed of a curable material coated or otherwise deposited on the substrate surface 12 to form a curable layer 24 and then cured to form the cured layer 20 on the substrate surface 12. The coated curable material is considered herein to be the curable layer 24 before it is cured and the cured layer 20 after it is cured. Similarly, a cured electrical conductor is an electrical conductor formed by locating a curable material, such as a conductive ink, in the micro-channel 60 and curing the curable material to form the conductive layer 54 in the micro-channel 60. As used herein, curing refers to changing the properties of a material by processing the material in some fashion, for example by heating, drying, irradiating the material, or exposing the material to a chemical, energetic particles, gases, or liquids.

The curable layer 24 is deposited as a single layer in a single step using coating methods known in the art, such as curtain coating. In an alternative embodiment, the curable layer 24 is deposited as multiple sub-layers using multi-layer deposition methods known in the art, such as multi-layer slot coating, repeated curtain coatings, or multi-layer extrusion coating. In yet another embodiment, the curable layer 24 includes multiple sub-layers formed in different, separate steps, for example with a multi-layer extrusion, curtain coating, or slot coating machine as is known in the coating arts.

Curable inks useful in the present invention are known and can include conductive inks having electrically conductive nano-particles, such as the silver nano-particles 90. In an embodiment, the electrically conductive nano-particles 90 are metallic or have an electrically conductive shell. The electrically conductive nano-particles 90 can be silver, can be a silver alloy, or can include silver. In various embodiments, cured inks can include metal particles 90, for example nano-particles 90. The metal particles 90 are sintered to form a metallic electrical conductor. The metal nano-particles 90 are silver or a silver alloy. Cured inks can include light-absorbing materials such as carbon black, a dye, or a pigment.

Curable inks provided in a liquid form, for example in an aqueous dispersion, are deposited or located in the micro-channels 60 and cured, for example by heating or exposure to radiation such as infra-red radiation, visible light, or ultra-violet radiation. The curable ink hardens to form the cured conductive ink that makes up the conductive layer 54. For example, a curable conductive ink with conductive nano-particles 90 is located within the micro-channels 60 and cured by heating or sintering to agglomerate or weld the nano-particles 90 together, thereby forming electrically conductive layer 54. Materials, tools, and methods are known for coating liquid curable inks to form multi-layer micro-wires 50.

In an embodiment, a curable ink can include conductive nano-particles 90 in a liquid carrier (for example an aqueous solution including surfactants that reduce flocculation of metal particles, humectants, thickeners, adhesives or other active chemicals). The liquid carrier is located in the micro-channels 60 and heated or dried to remove the liquid carrier or treated with hydrochloric acid, leaving a porous assemblage of conductive particles 90 that are agglomerated or sintered to form a porous electrical conductor in the cured layer 20. Thus, in an embodiment, curable inks are processed to change their material compositions, for example the conductive particles 90 in a liquid carrier are not electrically conductive but after processing form an assemblage that is electrically conductive.

Once deposited, the conductive inks are cured, for example by heating. The curing process drives out the liquid carrier and sinters the metal particles 90 to form a metallic electrical conductor that is the conductive layer 54. Conductive inks are known in the art and are commercially available. In any of these cases, conductive inks or other conducting materials are conductive after they are cured and any needed processing completed. Deposited materials are not necessarily electrically conductive before patterning or before curing. As used herein, a conductive ink is a material that is electrically conductive after any final processing is completed and the conductive ink is not necessarily electrically conductive at any other point in the micro-wire formation process.

The present invention is useful in a wide variety of electronic devices, including sensors, sensor devices, or other devices incorporating sensors.

The invention has been described in detail with particular reference to certain embodiments thereof, but it will be understood that variations and modifications can be effected within the spirit and scope of the invention.

PARTS LIST

B cross section line
C cross section line
5 imprinted electronic sensor structure
10 substrate
12 substrate surface
20 cured layer/first cured layer
22 layer surface
24 curable layer
30 curable conductive ink 32 cured conductive ink
40 environmental factor
42 first group of multi-layer micro-wires
44 second group of multi-layer micro-wires
50 multi-layer micro-wire
52 conductive layer depth
54 conductive layer
55 curable reactive material
56 reactive layer/second cured layer
57 reactive layer depth
58 inert layer
60 micro-channel
62 micro-channel depth
64 micro-channel bottom
66 micro-channel side
68 micro-channel width
69 micro-channel top width
70 radiation
80 controller
82 optical sensor
90 particle
100 provide substrate step
102 coat curable layer step
104 coat curable reactive material layer step
106 imprint curable layers step
108 cure curable layers step
110 provide micro-channels step
120 coat conductive material step
130 remove conductive material from substrate step
140 cure conductive material step
150 coat reactive material step
160 optional remove reactive material from substrate step
170 cure reactive material step
200 coat curable layer step
210 imprint curable layer step
220 cure curable layer step
250 expose reactive material step
260 provide electrical signal step
270 receive electrical signal step
280 analyze electrical signal step
290 identify environmental factor step

The invention claimed is:

1. A method of making an imprinted electronic sensor structure on a substrate for sensing an environmental factor, comprising:
coating a curable layer on the substrate, imprinting the curable layer to form micro-channels in the curable layer, and curing the curable layer to form a plurality of spatially separated micro-channels extending from the layer surface into the cured layer;
locating a first layer in the micro-channels, and locating a second layer at least partly over the first layer to form a multi-layer micro-wire in each micro-channel, wherein either:
the step of locating the first layer in the micro-channels includes forming a cured electrical conductor as a conductive layer located only within the micro-channel, and the step of locating the second layer at least partly over the first layer includes providing the second layer that is a reactive layer; or
the step of locating the first layer in the micro-channels includes providing the first layer as a reactive layer, and the step of locating the second layer at least partly over the first layer includes forming a cured electrical conductor as a conductive layer located only within the micro-channel;
forming an inert layer located between the conductive layer and the reactive layer, the inert layer preventing chemical reactions between the reactive layer and the conductive layer; and
exposing the reactive layer to the environmental factor and so that at least a portion of the reactive layer responds to the environmental factor.

2. The method of claim 1, wherein locating the first and second layers includes locating the first layer, curing the first layer, locating the second layer over the first layer, and curing the second layer so that the conductive layer is closer to the layer surface than the reactive layer.

3. The method of claim 1, wherein locating the first and second layers includes coating the substrate with the curable layer, coating the curable layer with a curable second layer, imprinting the curable layer and the second curable layer in a common step with a common imprinting stamp, and curing the curable layer and the second curable layer in a common step to form the micro-channels in the cured layer and the second layer, the second layer extending over the micro-channel bottom, the micro-channel sides, and the substrate surface outside the micro-channels.

4. The method of claim 1, wherein locating the first and second layers includes locating the first layer, curing the first layer, locating the second layer over the first layer, and curing the second layer so that the reactive layer is closer to the layer surface than the conductive layer.

5. The method of claim 4, wherein locating the second layer includes coating the second layer over the substrate surface and the micro-channels so that the reactive layer extends over the substrate surface outside the micro-channels.

6. The method of claim 1, wherein the inert layer includes gold.

7. The method of claim 1, further including functionalizing a surface of the inert layer to provide a reactive layer that is reactive to a specific environmental factor.

8. The method of claim 1, wherein the cured electrical conductor includes metal particles and further including coating a conductive ink in the micro-channels and curing the conductive ink.

9. The method of claim 1, wherein the micro-channels have a micro-channel bottom, a micro-channel top, and micro-channel sides and wherein the micro-channel walls are not perpendicular to the substrate surface.

10. The method of claim 9, wherein the micro-channel bottom has a surface area smaller than the surface area of the micro-channel top.

11. The method of claim 1, further including grouping the multi-layer micro-wires into a first group of multi-layer micro-wires and a second group of multi-layer micro-wires different from the multi-layer micro-wires of the first group, wherein the first group of multi-layer micro-wires is interdigitated with the second group of multi-layer micro-wires, the first group of multi-layer micro-wires are electrically connected and the second group of multi-layer micro-wires are electrically connected, and further including providing a controller for electrically controlling the first and second groups of multi-layer micro-wires.

12. The method of claim 11, further including using the controller to measure the electrical response of the first and second groups of multi-layer micro-wires, the electrical response including one or more of the amperometric response, the resistance, the capacitance, the impedance, the complex impedance, or the inductance.

13. The method of claim 1, wherein the environmental factor is a chemical, is heat, is moisture, is radiation, or is a biological material.

14. The method of claim 1, further including measuring a response of the reactive layer to the environmental factor.

15. The method of claim 14, wherein the reactive layer response is a change in conductivity, dielectric constant, absolute permittivity, or relative permittivity.

16. The method of claim 1, further including exposing the reactive layer to a liquid.

17. The method of claim 1, further including exposing the reactive layer to a gas.

18. The method of claim 1, further including providing an optical sensor for sensing the optical state of the multi-layer micro-wires and optically sensing the optical state of the multi-layer micro-wires.

19. The method of claim 1, further including measuring a first electrical response of the multi-layer micro-wire at a first time, measuring a second electrical response of the multi-layer micro-wire at a second time later than the first time, comparing the first electrical response to the second electrical response to determine a change in the environmental factor, to determine a concentration of the environmental factor, or to determine a change in the reactive layer in response to the environmental factor.

\* \* \* \* \*